United States Patent
Manhart (10) Patent No.: US 10,453,198 B2
(45) Date of Patent: Oct. 22, 2019

(54) DEVICE AND METHOD FOR DELINEATING A METAL OBJECT FOR ARTIFACT REDUCTION IN TOMOGRAPHY IMAGES

(71) Applicant: Michael Manhart, Fürth (DE)

(72) Inventor: Michael Manhart, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/458,206

(22) Filed: Mar. 14, 2017

(65) Prior Publication Data
US 2017/0270687 A1    Sep. 21, 2017

(30) Foreign Application Priority Data

Mar. 15, 2016   (DE) .......................... 10 2016 204 226

(51) Int. Cl.
*G06K 9/00*   (2006.01)
*G06T 7/11*   (2017.01)
(Continued)

(52) U.S. Cl.
CPC .............. *G06T 7/11* (2017.01); *A61B 6/5258* (2013.01); *G06T 11/008* (2013.01); *A61B 6/032* (2013.01);
(Continued)

(58) Field of Classification Search
CPC ..... A61B 6/032; A61B 6/5258; A61B 6/4085; A61B 6/4441; A61B 6/505;
(Continued)

(56) References Cited

U.S. PATENT DOCUMENTS

2003/0156684 A1* 8/2003 Fessler .................. A61B 6/032
378/210
2007/0172105 A1* 7/2007 Bahlmann ................ G06K 9/00
382/131
(Continued)

FOREIGN PATENT DOCUMENTS

DE    102011075912 A1    11/2012
DE    102013218819 B3    10/2014

OTHER PUBLICATIONS

Besag, J. "On the Statistical Analysis of Dirty Pictures", in: Journal of the Royal Statistical Society. Series B, vol. 48, No. 3, pp. 259-302 (1986).
(Continued)

*Primary Examiner* — Avinash Yentrapati
(74) *Attorney, Agent, or Firm* — Lempia Summerfield Katz LLC (57) ABSTRACT

A method for delineating a metal object for artifact reduction in tomography images is provided. Projection images of a body containing the metal object are received and a volume model of the body is formed on the basis of the projection images. Voxels that are part of a region encompassing the metal object and at least one metal artifact are chosen in the volume model on the basis of segmentation criterion and combined to form a first volume mask. The first volume mask is projected onto the projection images and a respective projection mask is generated. The projection masks are is altered on the basis of pixel values of the projection images. A second volume mask is determined from the altered projection masks. The second volume mask is altered on the basis of voxel values of the volume model and the altered volume mask is supplied as a description of the metal object.

14 Claims, 4 Drawing Sheets

(51) Int. Cl.
*A61B 6/00* (2006.01)
*G06T 11/00* (2006.01)
*A61B 6/03* (2006.01)
*A61B 6/12* (2006.01)

(52) U.S. Cl.
CPC ............... *A61B 6/12* (2013.01); *A61B 6/4441* (2013.01); *A61B 6/5205* (2013.01); *G06T 2207/10081* (2013.01)

(58) Field of Classification Search
CPC . G06T 2207/10081; G06T 5/002; G06T 5/50; G06T 11/005; G06T 11/008; G06T 2200/04; G06T 2207/20061; G06T 2207/20224; G06T 2207/30008; G06T 2207/30016; G06T 2207/30101; G06T 7/12; G06T 7/174
See application file for complete search history.

(56) References Cited

U.S. PATENT DOCUMENTS

| | | | | |
|---|---|---|---|---|
| 2010/0082692 | A1* | 4/2010 | Akinyemi | G06K 9/469 707/797 |
| 2011/0081071 | A1* | 4/2011 | Benson | G06T 11/005 382/154 |
| 2013/0039556 | A1* | 2/2013 | Kachelriess | A61B 6/00 382/131 |
| 2014/0363067 | A1* | 12/2014 | Stayman | G06T 11/005 382/131 |
| 2015/0029178 | A1* | 1/2015 | Claus | A61B 6/032 345/419 |
| 2015/0078507 | A1* | 3/2015 | Kyriakou | A61B 6/4085 378/4 |
| 2015/0279084 | A1* | 10/2015 | Deuerling-Zheng | G06T 5/002 345/424 |
| 2016/0078647 | A1* | 3/2016 | Schildkraut | G06T 11/005 382/131 |
| 2016/0117850 | A1* | 4/2016 | Jin | A61B 6/03 382/131 |
| 2016/0180554 | A1* | 6/2016 | Brendel | G06T 11/005 382/131 |
| 2016/0324499 | A1* | 11/2016 | Sen Sharma | A61B 6/5258 |
| 2016/0343127 | A1* | 11/2016 | Miller | A61B 5/055 |
| 2016/0371862 | A1* | 12/2016 | Silver | G06T 11/008 |
| 2017/0150937 | A1* | 6/2017 | Stille | A61B 6/5258 |

OTHER PUBLICATIONS

German Office Action for related German Application No. 10 2016 204 226.2 dated Nov. 24, 2016, with English Translation.

Jin, Pengchong et al: "Joint Metal Artifact Reduction and Segmentation of CT Images Using Dictionary-Based Image Prior and Continuously-Relaxed Potts Model", in: Proceedings of the IEEE International Conference on Image Processing, 2015, ICIP 2015, pp. 798-802.

Prell D. et. al.: "A novel forward projection-based metal artifact reduction method for flat-detector computed tomography", in: Phys. Med. Biol. 54, pp. 6575-6591, (2009).

Stille, Maik et al: "Metal artifact reduction by projection replacements and non-local prior image integration", in: Current Directions in Biomedical Engineering 1, 2015, pp. 100-103.

Veldkmap, W. et. al.: "Development and validation of segmentation and interpolation techniques in sinograms for metal artifact suppression in CT", in: Medical Physics 37, 620 (2010); doi: 10.1118/1.3276777.

Wang, G. et. al.: "Iterative Deblurring for CT Metal Artifact Reduction", in: IEEE Transactions on Medical Imaging, vol. 15, No. 5, pp. 657-664 (1996).

Yuki, I. et. al.: "High-Resolution C-Arm CT and Metal Artifact Reduction Software: A Novel Imaging Modality for Analyzing Aneurysms Treated with Stent-Assisted Coil Embolization", in: AJNR Am J Neuroradiol, published Sep. 10, 2015 as 10.3174/ajnr.A4509.

European Search Report for related European Application No. 17161123.9 dated Aug. 22, 2017.

Mehranian et al.: "3D Prior Image Constrained Projection Completion for X-ray CT Metal Artifact Reduction"; in: IEEE Transactions on nuclear science; vol. 60; No. 5; pp. 3318-3332; Oct. 2013.

* cited by examiner

DEVICE AND METHOD FOR DELINEATING A METAL OBJECT FOR ARTIFACT REDUCTION IN TOMOGRAPHY IMAGES

CROSS REFERENCE TO RELATED APPLICATIONS

This application claims the benefit of DE 102016204226.2 filed on Mar. 15, 2016, which is hereby incorporated by reference in its entirety.

TECHNICAL FIELD

Embodiments relate to a method and device for delineating a metal object for artifact reduction in tomography images.

BACKGROUND

Projection images of a body are used for generating tomography images. The projection images may be generated by a projection device, for example a computer tomograph (CT). The body may be a human, animal, or an object. A volume model of at least part of the body is formed on the basis of the projection images. A sectional view of the volume model represents a tomography image or a tomogram.

If there is a metal object in the body, for example a metal clip, the volume model may include metal artifacts. Individual voxels (volume elements) of the volume model in the immediate vicinity of the metal object do not describe the property of the body tissue located there but may be, depending on overexposure or underexposure, have voxel values that are very similar to the voxel values of the metal object. The individual voxels may not be distinguishable.

A scientific publication by Veldkamp et al. (W. J. H. Veldkamp, R. m. S. Joemai, A. J. van der Molen, J. Geleijns, "Development and validation of segmentation and interpolation techniques in sinograms for metal artifact suppression in CT", Medical Physics 37, 620 (2010)) discloses a method for reducing metal artifacts.

The form of the metal object may be determined by using the method or by manual marking the metal object in a tomography image. The form may be considered when calculating a volume model. The effect of the metal object on the voxels in the vicinity is reduced in the volume model.

SUMMARY AND DESCRIPTION

Embodiments provide a device and a method for artifact reduction of a metal object in tomography images in which the metal object may be automatically delineated or described.

Embodiments provide a method for delineating a metal object. The delimitation provides an artifact reduction that is carried out in tomography images using available methods. A description of the three-dimensional form of the metal object may be used, however, and may accordingly be provided in an automated manner.

The projection images of a body containing the metal object are received from a projection device. The projection device may be, for example, a computer tomograph that generates the projection images based on X-rays or based on a positron emission. The projection device may be, for example, an X-ray C-arm system. The projection images contain pixels (image elements) that each have a pixel value that indicate, for example, a damping property of the body in respect of the radiation used by the projection device. The unit of a pixel value may be, for example, HU (Hounsfield Unit).

A volume model of the body is formed based on the projection images. The volume model has individual voxels (volume elements). Each voxel indicates using a voxel value, a respective damping property of the voxel with respect to the radiation of the projection device. A method for generating a volume model of this kind is filtered back projection.

In the volume model, the metal object may cause metal artifacts, for example a star-shaped region around the actual metal object. The voxels of this star-shaped region have almost the same voxel values as the voxels of the metal object itself. To be able to recognize the voxels of the metal object itself, the following method is provided.

In the volume model, voxels, that according to the segmentation criterion, are part of the metal object and are metal artifacts, are chosen based on a segmentation criterion and combined to form a volume mask. The segmentation criterion may provide or use, for example, threshold value detection for the pixel values. All of the voxels with voxel values that are greater or smaller than a predetermined threshold value are associated with the metal object. The voxels form the volume mask. Such a volume mask represents a cohesive region. This first volume mask is projected onto the projection images. The projection represents a projection mask for the respective projection image. Forward projection may be used to project the first volume mask. Forward projection alters the process of projection and may be carried out by the projection device. A projection mask depicts the shadows of the first volume mask on the respective projection image.

Each projection mask is altered on the basis of pixel values of the respective projection images. The projection images are artifact-free, i.e. pixel values of pixels that are adjacent to the projection of the metal object are not affected. While the metal object may not be distinguished so clearly from, for example, bones in the projection images, the position of the metal object is known, however, through the projection mask.

A second volume mask is determined from the altered projection masks. The determination is based on, for example, back projection. The second volume mask describes a region within the metal artifacts in the volume but still surrounds the voxels of the metal object. The second volume mask is altered on the basis of voxel values of the volume model. A distinction may be made between the voxel values of the metal object itself and the (similar) voxel values of the metal artifacts using the second volume mask. A distinction may be made, for example, between voxel values outside of the volume mask but that are still located within the metal artifacts, and voxel values within the volume mask. The altered volume mask is provided as the description of the three-dimensional form of the metal object.

A final volume model may be formed from the projection images based on the altered volume mask. The altered volume mask may be used, for example, to hide or ignore the pixel values of pixels of the projection images that represent the metal object. The tomography images may be formed from the final volume model as sectional views.

Embodiments provide that a metal object is detected in the first volume model where the metal object clearly differs by virtue of its voxel values from voxel values of the tissue and bones of the body. However, the exact form or the limits of the metal object may be falsified due to the metal artifacts in the volume model. The respective projection mask may be refined or altered as a result of the projection masks in the projection images using the artifact-free pixel values. The masks may be projected back to the volume where the second volume mask is produced that provides a more precise distinction to be made between the voxel values of the metal object and the voxel values of the volume background (i.e. the surroundings of the metal object) affected by the artifact. The altered volume mask is produced. The analysis in the volume model (clear metal object) is combined with the the projection images (artifact-free image).

Embodiments relate to altering the projection masks in the projection images. In an embodiment, the projection maks is altered so that a region containing the projection mask is delineated in the respective projection image. The region is larger than the projection mask. The region may be, for example, a rectangular region in which the projection mask is located. A bounding box may be used.

A metal allocation function of pixel values to the metal body and a background allocation function of pixel values to a metal-free image background is determined from pixel values of pixels of the region. Each allocation function describes whether for possible pixel values in each case, i.e., for example pixel values from a value interval, the respective pixel value is representative or typical for the metal body or the metal-free image background. The description may be a binary allocation (0 or 1) or a multi-valued indication, for example a probability or a percentage. For each pixel of the region, the affiliation to the projection mask is defined using the pixel's respective pixel value and on the basis of the two allocation functions (metal allocation function and background allocation function). The projection mask describes the pixels that are regarded as pertaining to the metal object. A distinction may be made between pixel values of the metal body and pixel values of the metal-free image background in the artifact-free projection images for one region in each case on the basis of the pixel values contained therein. Providing a region that is smaller than the overall projection image, but larger than the projection mask, prevents the large number of metal-free pixel values predominating statistically and therefore falsifying the distinction.

One or both allocation functions are each, for example, log-likelihood functions. The affiliation of each pixel to the projection mask is defined in that the respective log-likelihood value for metal and background is determined from its pixel value and the log-likelihood values are compared. If the log-likelihood value for metal is greater than that for the image background, the pixel is associated with the projection mask. Otherwise the pixel is excluded from the projection mask. A statistically optimal distinction may be determined between statistically distributed, for example Gaussian distributed, pixel values of two different groups (metal and image background).

An embodiment provides that the metal allocation function is determined on the basis of a statistical mean and/or a statistical variance of the pixel values of the pixels encompassed by the projection mask. The knowledge, represented by the projection mask, about the pixel values of the metal object is represented statistically by the mean $\mu_M$ and/or the variance $\sigma_M$ and used in the current iteration when allocating the pixels. Additionally, or alternatively, the background allocation function may also be determined on the basis of a statistical mean $\mu_B$ and/or a statistical variance $\sigma_B$ of the pixel values of the pixels excluded from the projection mask. The statistic of the pixel values of the image background, as is described by the current projection mask, is used.

An embodiment provides that one or both allocation functions are each formed based on an edge detection. The edges of the metal object that may be seen in the projection images are used to correctly classify the pixels as metal or image background.

An embodiment provides that a vicinity description is considered in each case by way of one or both allocation functions for each pixel position. A single pixel alone may not make up the metal object. Instead adjacent pixels may be present that belong to the metal object. The vicinity description is dependent on a number of adjoining pixels that are encompassed by the projection mask (pixels of the metal object) and a number of adjoining pixels (image background) that are excluded from the projection mask. The vicinity description is implemented, for example, as a region-growing for the projection mask or for the inverse projection mask. In an embodiment, the vicinity description is determined by smoothing the current projection mask. For example, a two-dimensional Gaussian filter or a different two-dimensional low-pass filter may be used. The filter may be applied to the projection mask.

An embodiment provides that one or both allocation functions are each formed as a function of the original or non-altered projection mask. The characteristic or the form of the initial projection mask formed directly by projection of the first volume mask is considered. The initial information (a-priori information) is retained. A degeneration of the shape of the projection mask, i.e. a change in shape that is independent of the metal object, is prevented.

The parameters that may be considered in the allocation functions, may be combined, for example, as a weighted sum.

The altered projection masks are merged again to form the second volume mask. The second volume mask may in each case be refined or altered by carrying out comparable steps in the volume model, as are described in connection with altering the (two-dimensional) projection masks. A region containing the second volume mask may be delineated in the volume model. The region is larger than the second volume mask and may be smaller than the overall volume model.

A volume based metal allocation function of voxel values to the metal body and a volume-based background allocation function of voxel values to a metal-free volume background is determined from voxel values of the voxels of the region. For example, the two volume-based allocation functions are each a log-likelihood function. The affiliation of each voxel to the second volume mask (i.e. the voxel is regarded as pertaining to the metal object) is defined based on a comparison of the log-likelihood values for metal and volume background determined from its voxel value. The described image background and the described volume background each describe metal-free body tissue or, for example, bones. In each iteration for each voxel of the region the affiliation thereof to the second volume mask is defined again using a respective voxel value on the basis of the two allocation functions (volume-based metal allocation function and a volume-based background allocation function).

The volume-based metal allocation function may also be determined using a statistical mean $\mu_M$ and/or a statistical variance $\sigma_M$ of the voxel values of the voxels encompassed by the second volume mask. Additionally, or alternatively, the volume-based background allocation function may be determined using a statistical mean $\mu_B$ and/or a statistical variance $\sigma_B$ of the voxel values of the voxels excluded from the second volume mask.

The volume-based allocation functions may also each be formed using an edge detection. Edges may denote surfaces that are identified by a pre-determined minimum contrast of the adjoining voxel values.

One or both volume-based allocation functions may each also consider a vicinity description for each voxel position. The vicinity description is dependent on a number of adjoining voxels (metal voxels) that are encompassed by the second volume mask and on a number of adjoining voxels (background voxels) that are excluded from the second volume mask. The vicinity description may be determined by smoothing the current volume mask. Three-dimensional low-pass filters may be used, for example a three-dimensional Gaussian function. Smoothing may be carried out in the two-dimensional and three-dimensional cases respectively by convolution.

To avoid degeneration of the second volume mask during the iterations, one or both volume-based allocation functions are each formed as a function of the non-altered second volume mask. The initial, original second volume mask is considered.

The parameters of the volume based allocation functions may also be combined, for example, as a weighted sum.

In an embodiment, a device is provided for delineating a metal object in a volume model formed from projection images of a body contained in the metal object. The device has a receiving device for receiving the projection images and a processor device. The receiving device may include, for example, a reading device for reading a storage medium on which the projection images are stored. The receiving device may also be, for example, a connector device for connecting the described projection device, i.e. for example for connecting a computer tomograph. The processor device includes program code that is configured to implement an embodiment of the method when run by the processor device.

The scope of the present invention is defined solely by the appended claims and is not affected to any degree by the statements within this summary. The present embodiments may obviate one or more of the drawbacks or limitations in the related art.

DETAILED DESCRIPTION

Figure 1:
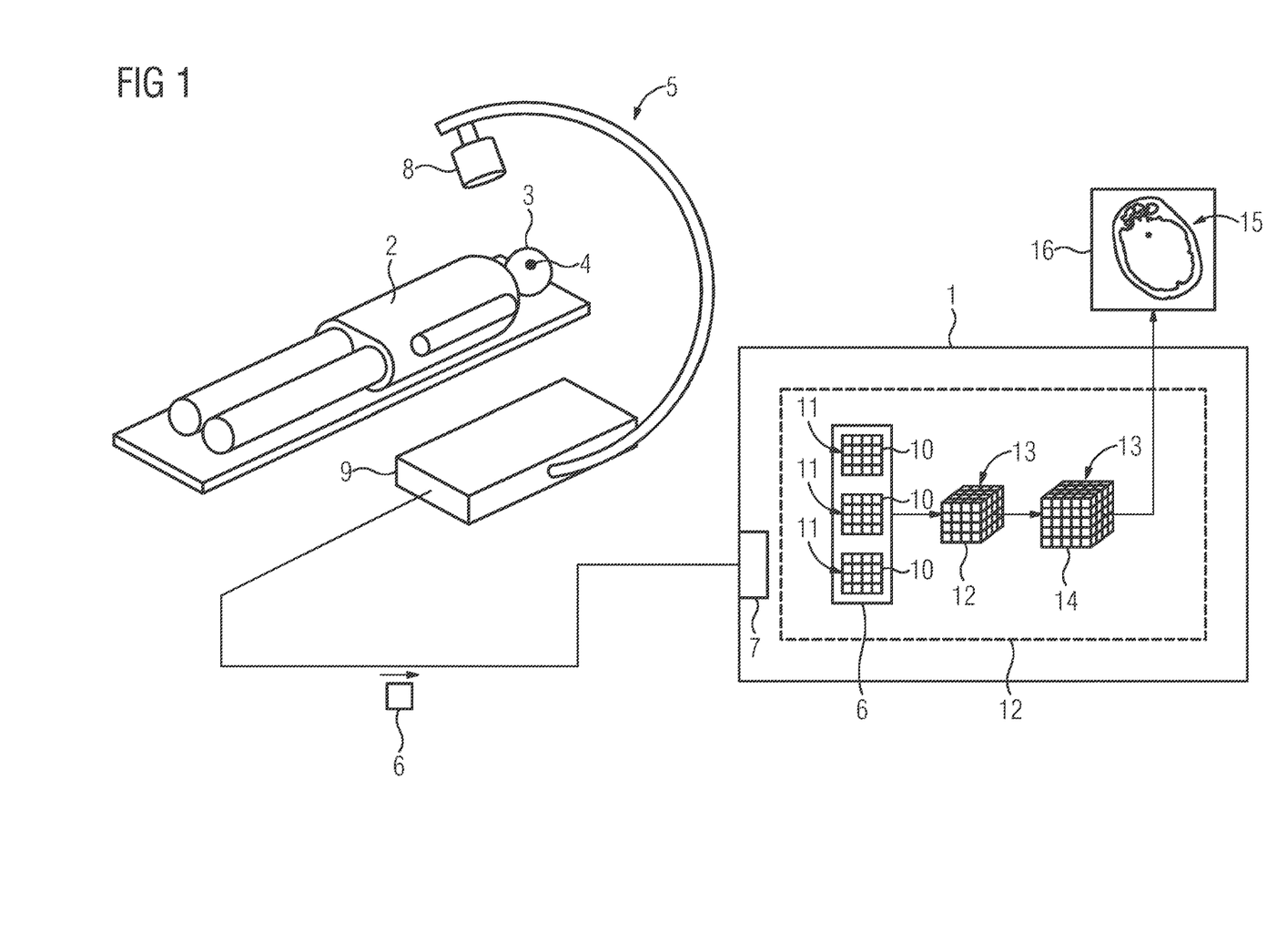
FIG. 1 depicts a schematic diagram according to an embodiment.

FIG. 1 depicts a device 1 that may examine a body 2 of a patient. For example, the head 3 may be examined. A metal object 4 may be present in the head 3 or in the body 2. The metal object may disrupt imaging of the body 2.

For imaging the body 2, for example the head 3, the device 1 may be coupled to a projection device 5 that may be, for example, a computer tomograph, e.g. an X-ray C-arm system. The device 1 may receive image data 6 from the projection device 5. A corresponding receiver or receiving device 7 may be provided in the device 1 to receive the image data 6. The receiving device 7 may receive the image data 6 from the projection device 5, for example directly via a cable or radio link, or read the image data 6 form a storage medium that stores the image data 6.

For generating the image data 6, the projection device 5 may irradiate the body 2, for example the head 3, with X-ray radiation by an X-ray source 8, so that the body 2 with the metal object 4 contained therein is imaged on an X-ray detector 9 as a projection.

The image data 6 includes projection images 10 from different irradiation angles or projection angles. Each of the projection images 10 in turn includes individual pixels 11, which have pixel values that describe damping of the radiation of the projection device 5 caused by the body 2.

The device 1 may have a processor device 12 that calculates a first volume model 12 from the projection images 10, for example using filtered back projection. The volume model 12 describes the part of the body 2 imaged in the projection images 10 three-dimensionally. The volume model 12 contains voxels 13 with voxel values that each describe the damping property of the body 2 in respect of the radiation of the projection device 5 for individual volume regions.

The processor device 12 carries out a method described below on the basis of the volume model 12, and this enables a final volume model 14 to be calculated whose voxels 13 have voxel values that have a lower artifact content of metal artifacts of the metal object 4 with respect to the voxels 13 of the first volume model 12. Tomography images 15 may be determined on the basis of the final volume model 14 and be displayed, for example, on a display device 16.

Figure 2:
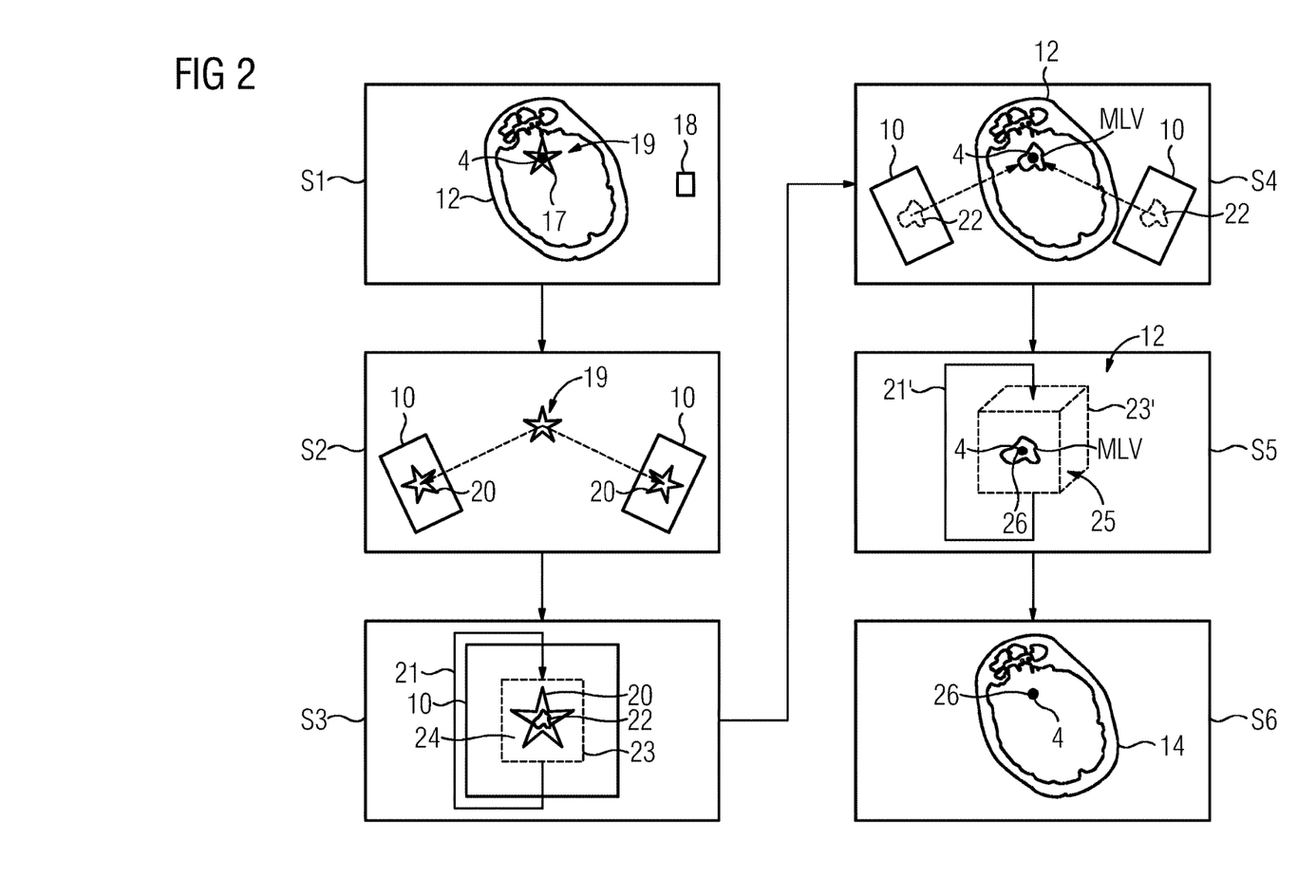
FIG. 2 depicts a flow diagram of a method according to an embodiment.

FIG. 2 depicts a method carried out by the processor device 12 for determining the final volume model 14. At act S1, the first volume model 12 is calculated from the projection images 10. The first volume model is represented in FIG. 2 by a single tomography image 15 that may be calculated from the volume model 12. Due to the metal object 4 the voxel values of the adjoining voxels 13 around the metal object are falsified, producing the illustrated metal artifacts 17. Voxels 13 pertaining to the metal object 4 and the metal artifacts 17 may be recognized or segmented on the basis of a segmentation criterion 18, i.e. may be distinguished from the remaining voxels 13 of the volume model 12. For example, a threshold value detection may be carried out. The voxels 13 selected or detected hereby form a first volume mask 19.

At act S2, an initial projection of the first volume mask 19 may occur, for example, on the basis of the known forward projection onto the projection images 10. The respective projection of the volume mask 19 is determined or delineated in the projection images 10. The pixels that represent the image or the projection of the volume mask 19 are identified in the projection images 10. A respective projection mask 20 is obtained in each projection image 10.

At act S3, an altered projection mask 22 is determined in each projection image 10, for example, on the basis of the respective pixels or image data of the respective projection image 10, in at least one iteration 21 from the respective projection mask 20. A region 23 that contains the projection mask 20 and part of an image background 24, is determined. The region 23 is larger, encompassing more pixels, than the projection mask 20 itself.

The respective altered projection masks 22 of the projection images 10 may be combined at act S4, for example using back projection, in the volume model 12 to form a second volume mask MLV that represents a three-dimensional, altered shape description of the metal object 4.

At act S5 the second volume mask MLV is altered in at least one iteration 21' on the basis of the voxel values of the voxels 13 of a region 23' of the volume 12. The region 23' is larger than the second volume mask MLV, e.g. contains more voxels. In addition to the volume mask MLV the alteration produces a metal-free volume background 25. An altered volume mask 26 is produced as a result of the at least one iteration 21'. The altered volume mask 26 describes the form of the metal object 4 more accurately than the initial volume mask 19.

At act S6 the final volume model 14 may be calculated based on the shape description of the metal object 4, e.g. based on the altered second volume mask 26.

Figure 3:
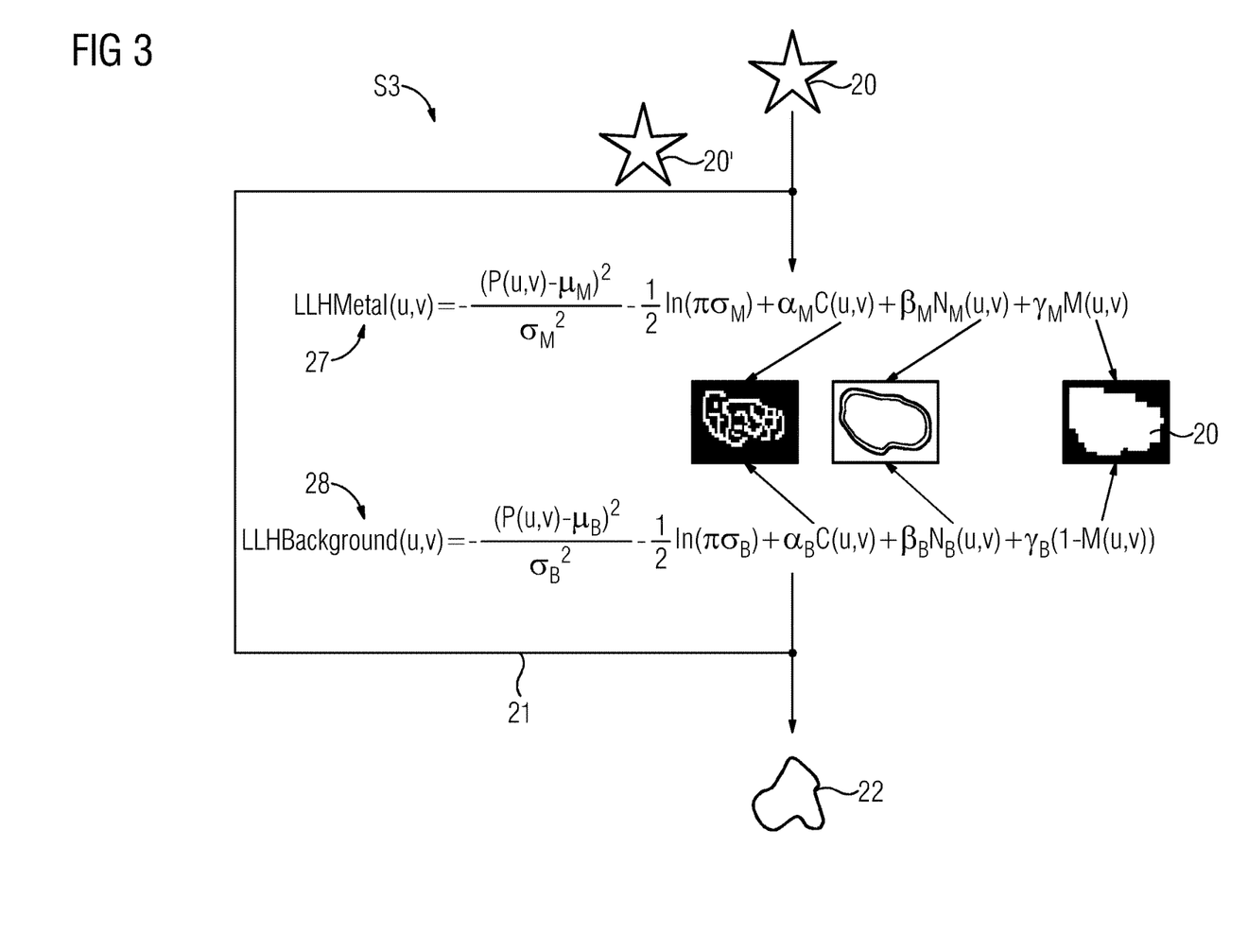
FIG. 3 depicts an example altered projection mask.

FIG. 3 depicts in relation to act S3 how the altered projection mask 22 may be determined from the projection mask 20 using at least one iteration 21.

A statistical mean $\mu_M$ (M-metal) and a variance $\sigma_M$ may be determined for pixel values P(u, v) that are located within the current projection mask 20' taken as a basis in the current iteration 21. The coordinates u, v each indicate the position of the pixel with the pixel value P in the projection image 10. In addition, edge information C(u, v) may be considered. The edge detection may be determined, for example, based on the Canny edge detection algorithm. A vicinity description $N_M$(u, v) may also be considered. In addition, the initial projection mask 20, M(u,v) may be used, where M(u, v) represents the binary indication (0/1) relating to the affiliation with the initial projection mask 20. The described parameters may be combined by weighting factors $\alpha_M$, $\beta_M$, $\gamma_M$ in the manner illustrated in FIG. 3. A metal allocation function 27 LLHMetal(u, v) is determined that represents a log-likelihood function.

The metal allocation function 27 may be supplemented by a background allocation function 28, LLHBackground(u,v), that may represent a log-likelihood function. The image background allocation function 28 produces a log-likelihood value LLHBackground(u, v), for each pixel, that may be formed based on the following parameters. A mean $\mu_B$ and a variance $\sigma_B$ may be determined from the pixel values P(u, v) of the pixels that are located outside of the current projection mask 20'. The edge detection may be used again with the edge information C(u, v) and/or an inverse vicinity description $N_B$ and/or the inverse of the initial projection mask 20, calculated by 1−M(u, v).

For forming the projection mask 20' of the subsequent iteration, the respective functional value of the two allocation functions 27, 28 is determined for each pixel based on a pixel value P(u, v) and the projection mask 20' determined from the pixels for which the following applies:

LLHMetal(u,v)>LLHBackground(u,v).

The projection masks 20, 20', 22 may be binary masks (mask values of the masks: 0 or 1).

The number of iterations 21 may be predefined and number in a range from 1 to 20. A stop criterion may be used, for example the minimum change in the projection mask 20' in a number of pixels. The altered projection mask 22 is produced after the end of the last iteration 21.

Figure 4:
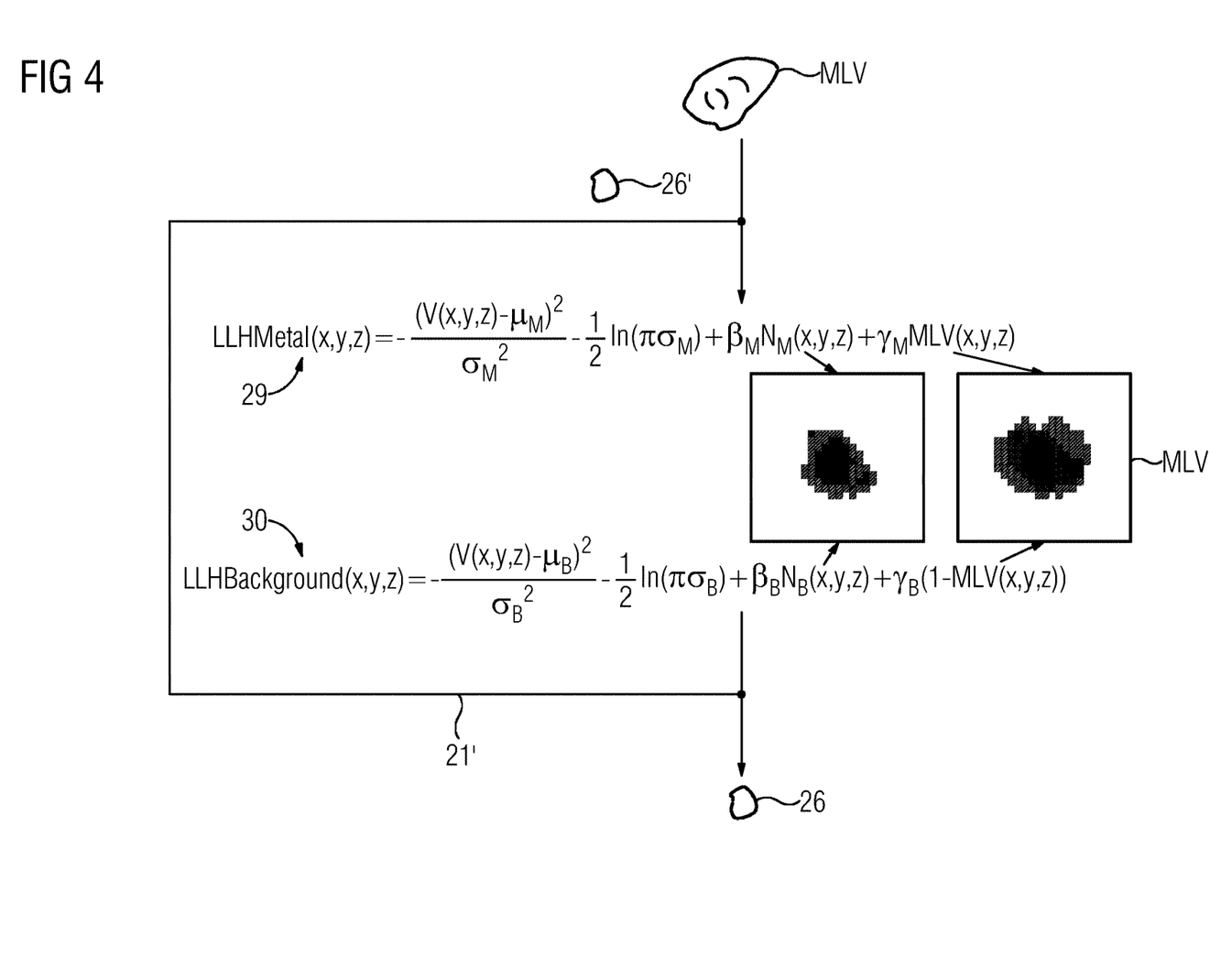
FIG. 4 depicts an example volume mask as iteratively altered.

Similar to FIG. 3, FIG. 4 depicts altering the second volume mask MLV in order to determine the altered volume mask 26. Each voxel of the region 23' has a voxel value V(x, y, z), where x, y, z represent the coordinates of the voxel in the volume model 12. A volume based metal allocation function 29, LLHMetal(x, y, z), and a volume based background allocation function 30, LLHBackground(x, y, z), may be determined for each voxel. The functions are also log-likelihood functions. A mean $\mu_M$ and a variance $\sigma_M$ of the voxel values of the voxels of the volume mask 26' may be determined on the basis of the current volume mask 26'. The described vicinity description $N_M$(x, y, z) and the initial volume mask MLV may be used as a basis again. The edge information C(x, y, z) may be used. Weighting factors $\beta_M$ and $\gamma_M$ may be provided for weighted combining of the parameters.

A mean $\mu_B$ and a variance $\sigma_B$ may be used for voxels outside of the current volume mask 26'. The inverse vicinity information $N_B$(x, y, z) and the inverse initial volume mask 1−MLV (x, y, z) may be used and a weighting $\beta_B$ and $\gamma_B$ may be used for combining the parameters.

The allocation of a voxel to the volume mask 26' and in the last iteration 21' to the volume mask 26 may occur by way of a comparison:

LLHMetal(x,y,z)>LLHBackground(x,y,z).

The volume masks MLV, 26' and 26 may be binary masks (voxel values of the masks: 0 or 1).

An embodiment may be carried out with minimial calculation effort as the considered regions 23, 23' are small in relation to the projection images 10 and the volume model 12. The considered regions, for example contain less than 20 percent, or for example less than 10 percent, of the pixels or voxels. The embodiment provides an automated reduction of metal artifacts by combined segmentation in the 3D volume domain and the projection domain.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for delineating a metal object for artifact reduction in tomography images, the method comprising:
   receiving, from a projection device, a plurality of projection images of a body containing the metal object;
   generating a volume model of at least part of the body using the plurality of projection images;
   selecting a plurality of voxels of the volume model, the plurality of voxels selected to be part of a region encompassing the metal object and at least one metal artifact based on a segmentation criterion, each of the plurality of voxels having a voxel value;
   combining the plurality of voxels and the at least one metal object into a first volume mask;
   projecting the first volume mask onto each of the plurality of projection images, the projecting resulting in a respective projection mask for each of the projection images;
   calculating a metal allocation log-likelihood value for each pixel in the respective projection mask using a statistical mean and a statistical variance of the pixel values of the pixels encompassed by the projection mask;

calculating a background allocation log-likelihood value for each pixel in the respective projection mask using a statistical mean and a statistical variance of the pixel values of the pixels excluded from the projection mask;

defining for each pixel of the region an affiliation to the projection mask based on a comparison of the metal and background allocation log-likelihood values;

altering each respective projection mask so that the region containing the projection mask is delineated in the respective projection image;

determining a second volume mask from the altered projection masks;

altering the second volume mask based on the plurality of voxel values of the volume model; and providing the altered second volume mask as a three-dimensional form of the metal object.

2. The method of claim 1, wherein the segmentation criterion is based on threshold value detection.

3. The method of claim 1, wherein the metal allocation log-likelihood value and the background allocation log-likelihood value are further calculated based on an edge detection.

4. The method of claim 1, wherein the metal allocation log-likelihood value and the background allocation log-likelihood value are further calculated using a vicinity description for each pixel position that is dependent on a number of adjoining pixels encompassed by the projection mask and a number of adjoining pixels excluded from the projection mask.

5. The method of claim 1, wherein metal allocation log-likelihood value and the background allocation log-likelihood value are further calculated based on a function of a non-altered projection mask.

6. The method of claim 1, wherein altering the second volume mask comprises:

altering in that in the volume model, a region containing the second volume mask is delineated;

determining a volume-based metal allocation function of voxel values to the metal body and a volume-based background allocation function of voxel values to a metal-free volume background from voxel values of voxels of the region; and defining for each voxel of the region the affiliation to the second volume mask using each voxel's respective voxel value, the volume based metal allocation function, and the volume based background allocation function.

7. The method of claim 6, wherein the volume based metal allocation function, the volume based background allocation function, or the volume based metal allocation function and the volume based background allocation function is a log-likelihood function.

8. The method of claim 6, wherein the volume based metal allocation function, the volume based background allocation function, or the volume based metal allocation function and the volume based background allocation function is determined based on a statistical mean or a statistical variance of the voxel values of the voxels encompassed by the second volume mask.

9. The method of claim 6, wherein the volume based metal allocation function, the volume based background allocation function, or the volume based metal allocation function and the volume based background allocation function is formed based on edge detection.

10. The method of claim 6, wherein the volume based metal allocation function, the volume based background allocation function, or the volume based metal allocation function and the volume based background allocation function consider a vicinity description for each voxel position, wherein the vicinity description is dependent on a number of adjoining voxels encompassed by the second volume mask and a number of adjoining voxels excluded from the second volume mask.

11. The method of claim 6, wherein the volume based metal allocation function, the volume based background allocation function, or the volume based metal allocation function and the volume based background allocation function are determined as a function of a non-altered second volume mask.

12. An apparatus for delineating a metal object in a volume model formed from a plurality of projection images of a body containing the metal object, the apparatus comprising:

a receiver configured to receive the plurality of projection images; and a processor configured to generate a volume model of at least part of the body using the plurality of projection images, select a plurality of voxels that are part of a region encompassing the metal object and at least one metal artifact based on a segmentation criterion, each of the plurality of voxels having a voxel value, the processor further configured to combine the selected plurality of voxels and the at least one metal object to form a first volume mask, project the first volume mask onto each of the plurality of projection images to generate respective projection masks, alter each respective projection masks so that the region containing the projection mask is delineated in the respective projection image, calculate a metal allocation log-likelihood value for each pixel in the respective projection mask using a statistical mean and a statistical variance of the pixel values of the pixels encompassed by the projection mask, calculate a background allocation log-likelihood value for each pixel in the respective projection mask using a statistical mean and a statistical variance of the pixel values of the pixels excluded from the projection mask, define for each pixel of the region an affiliation to the projection mask based on the metal allocation and background log-likelihood values, determine a second volume mask from the altered projection masks, alter the second volume mask based on the plurality of voxel values of the volume model, and provide the altered second volume mask as a three-dimensional form of the metal object.

13. The apparatus of claim 12, wherein the segmentation criterion is based on threshold value detection.

14. The apparatus of claim 12, wherein metal allocation log-likelihood value and the background allocation log-likelihood value are further calculated based on an edge detection.

* * * * *